United States Patent [19]

Zahradnik

[11] Patent Number: 4,935,339
[45] Date of Patent: Jun. 19, 1990

[54] DELAYED SOLID PHASE IMMUNOLOGIC ASSAY

[75] Inventor: Richard Zahradnik, San Juan Capistrano, Calif.

[73] Assignee: Nichols Institute Diagnostics, San Juan Capistrano, Calif.

[21] Appl. No.: 731,470

[22] Filed: May 7, 1985

[51] Int. Cl.$^5$ ............... G01N 33/531; G01N 33/536; G01N 33/543; G01N 33/577
[52] U.S. Cl. ........................................ 435/5; 435/7; 435/810; 436/501; 436/513; 436/518; 436/531; 436/538; 436/547; 436/548; 436/817; 436/824; 530/387; 530/413; 935/108; 935/110
[58] Field of Search .............. 436/513, 518, 531, 532, 436/541, 543, 548, 547, 809, 817, 824, 501, 938; 435/7, 810, 5; 530/387, 413; 935/108, 110

[56] References Cited

U.S. PATENT DOCUMENTS

| 3,720,760 | 3/1973 | Bennich et al. ..................... 436/513 |
| 3,853,987 | 12/1974 | Dreyer ................................. 424/1.1 |
| 3,995,019 | 11/1976 | Jerome ................................ 424/85 |
| 4,017,597 | 4/1977 | Reynolds ........................... 436/531 |
| 4,034,073 | 7/1977 | Weetall .............................. 436/500 |
| 4,200,436 | 4/1980 | Mochida et al. ................... 435/7 |
| 4,228,237 | 10/1980 | Hevey et al. ...................... 435/7 |
| 4,244,940 | 1/1981 | Jeong et al. ....................... 422/61 |
| 4,253,995 | 3/1981 | Katz .................................... 424/85 |
| 4,271,140 | 6/1981 | Bunting ............................. 436/820 |
| 4,289,747 | 9/1981 | Chu ..................................... 435/7 |
| 4,298,592 | 11/1981 | Lin et al. ........................... 436/540 |
| 4,298,685 | 11/1981 | Parikh et al. ...................... 435/7 |
| 4,315,907 | 2/1982 | Fridlender et al. ................ 435/7 |
| 4,343,896 | 8/1982 | Wolters et al. .................... 435/7 |
| 4,347,311 | 8/1982 | Schmitz ............................. 435/5 |
| 4,349,528 | 9/1982 | Koprowski et al. .............. 424/85 |

(List continued on next page.)

FOREIGN PATENT DOCUMENTS

| 105714 | 4/1984 | European Pat. Off. . |
| 0160900 | 11/1985 | European Pat. Off. . |
| 8500663 | 2/1985 | Int'l Pat. Institute . |
| 12074727 | 11/1981 | United Kingdom . |
| 2098730 | 11/1982 | United Kingdom . |
| 2152664 | 8/1986 | United Kingdom . |
| 84/04171 | 10/1984 | World Int. Prop. O. . |

OTHER PUBLICATIONS

B. Mattiason et al. in E. T. Maggio (ed.) *Enzyme-Immunoassay*, CRC Press, Boca Raton, FL., 1980, pp. 213-248.

(List continued on next page.)

*Primary Examiner*—Robert J. Warden
*Assistant Examiner*—David A. Saunders
*Attorney, Agent, or Firm*—Saidman, Sterne, Kessler & Goldstein

[57] ABSTRACT

A method for the determination of a substance present in a sample, which comprises:
(a) contacting a sample containing a substance with:
  (i) a first immunological binding partner to the substance, wherein the first immunological binding partner is a monoclonal antibody bound to biotin or a biotin-binding protein,
  (ii) a second immunological binding partner to the substance, wherein the second immunological binding partner is a detectably labeled region specific polyclonal antibody, and
  (iii) a biotin binding protein or biotin bound to a carrier;
(b) incubating the components of step (a) for a period of time and under conditions sufficient to form an immune complex between the substance, the first immunological binding partner, the second immunological binding partner, and the carrier;
(c) separating the carrier from the sample; and
(d) determining the detectably labeled second immunological binding partner in either the sample or the carrier;
wherein the reaction between the first immunological binding partner and the carrier occurs after, or substantially contemporaneously with, formation of an immune complex between the first immunological binding partner and the substance.

34 Claims, 3 Drawing Sheets

U.S. PATENT DOCUMENTS

| | | | |
|---|---|---|---|
| 4,360,592 | 11/1982 | Weltman et al. | 435/7 |
| 4,371,515 | 2/1983 | Chu | 436/544 |
| 4,376,110 | 3/1983 | David et al. | 435/7 |
| 4,376,165 | 3/1983 | Hornby et al. | 435/7 |
| 4,378,428 | 3/1983 | Farina et al. | 435/7 |
| 4,380,580 | 4/1983 | Boguslaski et al. | 435/7 |
| 4,383,031 | 5/1983 | Boguslaski et al. | 435/7 |
| 4,459,360 | 7/1984 | Marinkovich | 436/513 |
| 4,486,530 | 12/1984 | David et al. | 435/7 |
| 4,496,654 | 1/1985 | Katz et al. | 435/7 |
| 4,514,505 | 4/1985 | Canfield et al. | 436/500 |
| 4,624,930 | 11/1986 | Tanswell | 436/518 |

OTHER PUBLICATIONS

E. D. Sevier et al., *Clin. Chem.*, 27, 1797–1806, 1981.

A. Voller, *Diagnostic Horizons*, 2 (1), 1–7, 1978.

C. N. Hales et al., *Methods in Enzymology*, 70, 334–337, 1980.

A. Voller, in E. T. Maggio (ed.), *Enzyme-Immunoassay*, CRC Press, Boca Raton, FL., 1980, pp. 181–196.

Kwapinski, *The Methodology of Investigative and Clinical Immunology*, Robert E. Krieger Publishing Company, Inc., Malabar, FL., 1982, pp. 406–407.

Cooper-Biomedical Research Products, Catalogue of March 1, 1985, pp. 9, 10, 15.

Roitt, *Essential Immunology*, 5th Edition, Blackwell Scientific Publications, Oxford, 1984, pp. 21–46.

Antibodies: Their Structure and Function, M. S. Stewart, eds. W. J. Bramar and E. Edidin, Chapman and Hall, 1984, Section 4.3.1.

$^{125}$I-IgE Chromacode TM Radioimmunoassay Kit, Bio-RIA, Jan. 1981.

Beckman Epsilon TM IgE, Beckman Instructions 015-246167-A, 1983, Beckman Industries Inc.

Guesdon et al., *J. Histochem. Cytochem.* 27 (8): 1131–1139 (1979).

European Search Report for Application No. 86106173.7.

Steward and Steensgaard, *Antibody Affinity: Thermodynamic Aspects and Biological Significance* (CRC Press, Inc. 1983), pp. 6, 16–19, 48, 56–57.

Rattle, S. J. et al., Clinical Chemistry, 30/9: 1457 (1984).

DELAYED SOLID PHASE IMMUNOLOGIC ASSAY

BACKGROUND OF THE INVENTION

1. Field of the Invention

The present invention relates to an immunologic assay in which an antigen/antibody immune complex is formed and isolated through the use of a biotin/avidin association reaction.

2. Brief Description of the Background Art

Immunologic assays for the detection of antigenic substances or antibodies in specimens are well known. For example, Chu (U.S. Pat. No. 4,289,747) discloses an immunometric assay (also known as a "sandwich assay") for the detection of various substances in body fluids. The assay described in the Chu patent utilizes unrestricted polyclonal antisera from different species to form the sandwich with the particular antigenic substance. The sandwich is then removed from the solution via a lectin/sugar association reaction. The assay emphasizes taking advantage of the low binding affinity between lectin and sugar to allow reversible release of the immune complex from the solid phase to which the lectin or sugar is bound. The assays are described in the simultaneous, reverse, and forward modes.

Wolters, et al., U.S. Pat. No. 4,343,896, also describes a sandwich assay. The sandwich is formed in liquid phase between a particular antigen and antibodies raised to that antigen in two species. Reaction between these two groups of antibodies, one of which is labeled, and the antigen is allowed to occur in liquid phase before being exposed to a solid phase matrix to which is bound a second antibody (anti-globulin) reactive to the unlabeled species of antibody forming the immune complex.

In Parikh, et al., U.S. Pat. No. b. 4,298,685, a non-sandwich type assay is described which utilizes biotin and avidin. This patent discloses a competition assay wherein antigen which may be present competes with enzyme-labeled antigen for binding sites on biotinylated antibody. After incubation of these reagents, the liquid phase is exposed to a solid phase bound avidin to allow removal of the antibody/antigen complexes from the liquid phase.

Another example of a sandwich immunoassay is described in David, et al., U.S. Pat. No. 4,376,110. The assay disclosed here uses two different monoclonal antibodies from two different hybridomas. The David technique involves one of the monoclonal antibodies being bound to the solid phase throughout the assay, rather than being used in a homogeneous phase. The solid phase monoclonal antibody 1 is reacted with the liquid phase to detect the possible presence of antigen. A monoclonal antibody 2, which is labeled and soluble in liquid phase, will form, in the presence of antigen, a sandwich between solid phase monoclonal antibody 1, antigen, and labeled monoclonal antibody 2.

Katz, et al., U.S. Pat. No. 4,496,654, describe a method which utilizes the biotin-avidin reaction to strongly bind antibody to a solid phase substrate. This patent discloses coating an avidinated solid phase with biotinylated antibody for a specific antigen. This antibody-coated solid phase is then reacted with a sample containing the specific antigen and soluble labeled antibody to the specific antigen. After incubation, the labeled antibody bound to the solid phase or remaining in solution is measured.

In Gallati, et al., United Kingdom Patent Application GB No. 2,074,727A, sandwich assays are described which may occur in liquid phase between (1) two monoclonal antibodies specific for two different epitopes of the same antigen, (2) a monoclonal antibody and polyclonal antibodies raised in another species to the same antigen, and (3) polyclonal antibodies raised in two different species and being directed towards different epitopes of the same antigen.

An assay for the determination of allergen-specific human IgE is disclosed in Bennich, et al., U.S. Pat. No. 3,720,760. This patent described an assay in which a sample is exposed first to a solid phase to which is bound a specific allergen, followed by addition of a radioactively iodinated anti-globulin to human IgE.

The previously described immunoassays fall into two main categories. First, there are those immunoassays (David, Bennich, Katz) wherein one of the binding pair, either an antigen or an antibody, is attached to a solid phase, and a second binding partner, which is labeled, usually an antibody, is in the liquid phase. If the specimen contains the substance to be detected, then a complex is formed composed of the solid phase first binding partner, the substance being detected, and the detectably labeled second binding partner. In the second category (Chu, Wolters, Gallati) are those immunoassays wherein the first and second binding partners both react freely in the liquid phase to form an immune complex if the specimen contains the substance to be detected. This immune complex is then removed from the liquid phase by binding of one of the binding partners to a carrier which is modified such that it will bind the immune complex. This second type of immunoassay wherein initially neither binding partner is bound to a solid phase will be denominated herein as Delayed Solid Phase (DESP).

One of the major, problems with prior art DESP assays is that the systems use non-restricted polyclonal antibodies as the first and second binding partners in liquid phase. As a consequence, these two populations of antibodies will often compete for the same binding sites (epitopes) on the antigen in solution and thus lower the overall sensitivity of the assay. An additional problem with these prior art DESP immunoassays is that the ligand reaction used to remove the immune complex from solution is of low to moderate affinity.

None of the DESP assays described in the prior art disclose a system utilizing a monoclonal antibody as a first binding partner and a detectably labeled second binding partner, which is either a different monoclonal antibody or a polyclonal antibody of restricted specificity, used in conjunction with a high affinity ligand for removal of the immune complex from the liquid phase.

SUMMARY OF THE INVENTION

In the invention, biotin or a biotin-binding protein is bound to the first binding partner which remains in solution throughout the first part of the assay. If the assay is performed such that the first binding partner is immobilized before reacting in liquid phase with the substance being detected and the second binding partner, the sensitivity of the assay is much less than if the biotinylated (or biotin-binding protein-bound) first binding partner and labeled second binding partner are free in solution to react with the substance being determined. Allowing these reagents to react in free solution allows better kinetics of reactivity and stereochemical access to binding sites on the substance being detected than in a solid phase system, where the reactants must kinetically migrate to the solid phase. Advantage is then taken of the high affinity and specificity of the biotin-/avidin reaction.

Thus, the present invention provides a method for the determination of a substance present in a sample, which comprises:

(a) contacting a sample containing said substance with:
  (i) a first immunological binding partner to said substance, wherein the first immunological binding partner is bound to biotin or a biotin-binding protein,
  (ii) a second immunological binding partner to said substance, wherein said second immunological binding partner is detectably labeled; and
  (iii) a biotin-binding protein or biotin bound to a carrier;
(b) incubating the components of step (a) simultaneously or separately for a period of time and under conditions sufficient to form an immune complex between the substance, said first immunological binding partner, said second immunological binding partner, and said carrier;
(c) separating said carrier from the sample; and
(d) determining the detectably labeled second immunological binding partner in either said sample or said carrier;

wherein the reaction between the first immunological binding partner and the carrier occurs after, or substantially contemporaneously with, formation of an immune complex between the first immunological binding partner and the substance.

In one embodiment of the invention, it has been discovered that a DESP assay utilizing a monoclonal antibody and a labeled region-specific polyclonal antibody was far more sensitive than similar assays using two different monoclonal antibodies to different epitopes, or than assays using only polyclonal antibodies as the first and second binding partners.

The same finding applies to a reaction wherein the first reagent or binding partner is not a monoclonal antibody, but an antigen such as, for example, an allergen and where the second binding partner is a polyclonal antibody specific for the class of antibody being detected.

BRIEF DESCRIPTION OF THE PREFERRED EMBODIMENTS

In the method according to the invention, a sample containing a substance to be detected is contacted with the first binding partner, the second binding partner, and a carrier to which is bound biotin or a biotin-binding protein. The substance which is to be detected can be either an antigen or an antibody. The first and second binding partners react with different regions of the substance such that both partners can bind to the substance. The first binding partner is bound to either biotin or a biotin-binding protein. This first binding partner is either an antibody, when the substance being tested for in the sample is an antigen, or a substance capable of being bound by antibody, when the substance being detected in the sample is an antibody. The second binding partner is a detectably labeled antibody which is specific for the substance being detected in the sample. The carrier will have bound to it biotin if the first binding partner has a biotin-binding protein attached to it, or a biotin-binding protein if the first binding partner has biotin bound to it.

It should be understood that the term biotin also encompasses derivatives of biotin, such as, for example, the N-hydroxysuccinamide ester of biotin. The term biotin-binding protein includes avidin, streptavidin, and the like.

The determination of a substance in a sample using the method according to the invention can be carried out in any of various embodiments.

In a first embodiment a sample is incubated with the first and second binding partners. Incubation is continued for a period of time sufficient to allow the substance in the sample and the first and second binding partners to react. After the first incubation, the carrier is added to the reaction mixture and allowed to incubate for a time sufficient to allow binding to occur between the carrier and the first binding partner. After the second incubation, the carrier is washed to remove any nonspecifically bound labeled antibody. The labeled antibody bound to the carrier or remaining in the sample is then measured. In carrying out such embodiment, the process comprises, in more detail:

(a) first forming a mixture of the sample with the first and second immunologic binding partners, and incubating the mixture for a time and under conditions sufficient to allow the substance in the sample being detected to react with the first and second immunologic binding partners;
(b) adding to the mixture after said incubation of step (a) the carrier to which is bound biotin or a biotin-binding protein and incubating the new mixture for a time and under conditions sufficient to allow binding to occur between the carrier and the first immunologic binding partner;
(c) separating the carrier from the mixture; and
(d) detecting either the labeled second binding partner bound to the carrier or detecting the second binding partner not associated therewith.

In a second embodiment, the sample is initially incubated with the carrier to which is bound biotin or a biotin-binding protein, after which the first and second immunological binding partners are added and an incubation is carried out. In carrying out such embodiment, the process comprises, in more detail:

(a) first forming a mixture of the sample with the carrier to which is bound biotin or a biotin-binding protein;
(b) adding to the mixture of step (a) the first and second immunologic binding partners and incubating the new mixture for a time and under conditions sufficient to allow the substance being detected to react with both binding partners and to allow binding to occur between the carrier and first binding partner;
(c) separating the carrier from the mixture; and
(d) detecting either the labeled second binding partner bound to the carrier or detecting the second binding partner not associated therewith.

In a third embodiment, the sample, the carrier to which is bound biotin or biotin-binding protein, and the first and second immunologic binding partners are incubated simultaneously. This incubation is done under conditions and for a period of time sufficient to allow the substance being detected to react with the first and second binding partners and to allow binding to occur between the carrier and the first binding partner.

In carrying out such embodiment, the process comprises, in more detail:
(a) simultaneously forming a mixture comprising the sample, the carrier to which is bound biotin or a biotin-binding protein, and the first and second immunologic binding partners;
(b) incubating the mixture of step (a) for a time and under conditions sufficient to allow the substance being detected to react with both binding partners and to allow binding to occur between the carrier and the first binding partner;
(c) separating the carrier from the mixture; and
(d) detecting either the labeled second binding partner bound to the carrier or detecting the second binding partner not associated therewith.

In a fourth embodiment, the sample is initially incubated with the carrier to which is bound biotin or a biotin-binding protein, and the first immunological binding partner. The carrier is then washed to remove all unbound materials. The second immunological binding partner is then added and allowed to incubate for a time sufficient to allow binding to occur between the substance being detected and the second immunologic binding partner. In carrying out such embodiment, the process comprises, in more detail:
(a) first forming a mixture of the sample with the carrier to which is bound biotin or a biotin-binding protein and the first immunologic binding partner, and incubating the mixture for a time and under conditions sufficient to allow the substance in the sample being detected to react with the first immunologic binding partner and to allow binding to occur between the carrier and the first immunologic binding partner;
(b) adding to the mixture of step (a) the second immunologic binding partner and incubating the new mixture for a time and under conditions sufficient to allow the substance being detected to react with second immunologic binding partner;
(c) separating the carrier from the mixture; and
(d) detecting either the labeled second binding partner bound to the carrier or detecting the second binding partner not associated therewith.

It should be stated that the above-mentioned embodiments can also be varied with respect to addition of the carrier to which is bound biotin or a biotin-binding protein. Thus, in the first mode, the carrier and first immunological binding partner could be added to the specimen before addition of the second immunological binding partner; in the second mode, the carrier and the second immunological binding partner could be added to the specimen before addition of the first immunological binding partner; in the third mode, the carrier could be added substantially contemporaneously with the addition of the first and second immunological binding partners; and in the fourth mode, the first immunological binding partner could be added to the specimen before addition of the carrier and the second immunological binding partner.

The specific concentrations of first and second immunological binding partners, the temperature and time of incubation, as well as other assay conditions, can be varied, depending on such factors as the concentration of the antigen in the sample, the nature of the sample, and the like. Those skilled in the art will be able to determine operative and optimal assay conditions for each determination by employing routine experimentation.

For example, the immunoassay may be run at 4°–37° C., preferably at 26° C., and each incubation step may be as long as 72 hours.

Other steps such as washing, stirring, shaking, filtering, or pre-assay extraction of antigen or antibody and the like may, of course, be added to the assays, as may be desired or necessary for a particular situation.

There are many carriers to which biotin or biotin-binding protein can be bound and which can be used in the present invention. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding biotin or biotin-binding protein, or will be able to ascertain such, using routine experimentation.

The first immunological binding partner can be one or more monoclonal antibodies, or a substance capable of being bound by antibody, and is bound to either biotin or a biotin-binding protein. Biotin can be bound to this partner by using techniques readily available in the prior art, for example, as described in U.S. Pat. No. 4,298,685.

The binding of avidin or another biotin-binding protein to the first binding partner can be easily performed using standard conjugation techniques such as those described in Guesdon, J. et al., *The Journal of Histochemistry and Cytochemistry*, 27: 1131–1139 (1979).

The second immunological binding partner is one or more monoclonal antibodies, region-specific polyclonal antibody, or a polyclonal antibody which is specific for the substance being determined in the specimen. This antibody is coupled with a detectable label such as an enzyme, radioactive isotope, fluorescent compound, chemiluminescent compound, or bioluminescent compound.

Those of ordinary skill in the art will know of other suitable labels for binding to the second partner, or will be able to ascertain such, using routine experimentation. Furthermore, the binding of these labels to the second binding partner can be done using standard techniques common to those of ordinary skill in the art.

One of the ways in which the second immunological binding partner in the immunoassay can be detectably labeled is by linking this binding partner to an enzyme. This enzyme, in turn, when later exposed to its substrate will react with the substrate in such a manner as to produce a chemical moiety which can be detected as, for example, by spectrophotometric or fluorometric means. Examples of enzymes which can be used to detectably label are malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of the second immunological binding partner can also be detected by labeling the second immunological binding partner with a radioactive isotope. The presence of the radioactive isotope could then be determined by such means as the use of a gamma counter or a scintillation counter. Isotopes which are particularly useful are $3_H$, $125_I$, $131_I$, $32_P$, $35_S$, $14_C$, $51_{Cr}$, $36_{Cl}$, $57_{Co}$, $58_{Co}$, $59_{Fe}$, and $75_{Se}$.

It is also possible to detect the presence of the second binding partner by labeling the second binding partner with a fluorescent compound. When the fluorescently labeled second binding partner is exposed to light of the proper wavelength, its presence can then be detected due to fluorescence of the dye. Among the most important fluorescent labeling compounds are fluorescein isothiocyanate, rhodamine, phycoerythrin, phycocyanin, allophycocyanin, o-phthaldehyde, and fluorescamine.

Another way in which the second immunological binding partner can be detectably labeled is by coupling it to a chemiluminescent compound. The presence of the chemiluminescent-tagged immunological binding partner is then determined by detecting the presence of luminescence that arises during the course of a chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used to label the second immunological binding partner. Bioluminescence is a special type of chemiluminescence which is found in biological systems and in which a catalytic protein increases the efficiency of the chemiluminescent reaction. The presence of a bioluminescent second binding partner would be determined by detecting the presence of luminescence. Important bioluminescent compounds for purposes of labeling are luciferin, luciferase, and aequorin.

For purposes of the invention, the substance which is being detected by the immunoassay may be present in biological fluids and tissues, as well as samples derived from environmental and ecological sources.

Any sample containing a detectable yet unknown amount of antigen or antibody can be used. Normally, the sample is a liquid (such as, for example, urine, saliva, cerebrospinal fluid, blood, serum and the like) or solid or semi-solid (such as, for example, tissues, feces, and the like).

In the method of the present invention, if the first and second binding partners are antibodies, then the substance being detected would possess at least two epitopic determinants. The first, or first group, of these determinants would be bound by the first binding partner and the second, or second group, of these determinants would be bound by the second binding partner.

When the present invention is run in the format wherein only the second binding partner is an antibody, then the substance being detected in the sample need have only one epitopic determinant specific for the second binding partner.

The term "epitope" as used in this invention is meant to include any determinant responsible for specific interaction with an antibody molecule. Epitopic determinants usually consist of chemically active surface groupings of molecules such as amino acids or sugar side chains and have specific three dimensional structural characteristics as well as specific charge characteristics.

Monoclonal antibodies when used in the present invention can be produced in various ways using techniques well understood by those having ordinary skill in the art and will not be repeated here. Details of these techniques are described in such books as *Monoclonal Antibodies-Hybridomas: A New Dimension in Biological Analysis*, edited by Roger H. Kennett et al., published by Plenum Press (1980).

In the method of the invention, the immunoassay may also be performed using first and second monoclonal antibodies derived from either the same cell line or different cell lines. When the antibodies are derived from the same cell line, then they are identical with respect to binding specificity. However, when the first and second antibodies are derived from different cell lines, then the specificity in each case will be directed towards a different epitope on the substance being detected.

The term "region-specific polyclonal antibody" as used in the present invention to describe the second immunological binding partner means a polyclonal antibody which has been pre-absorbed or purified such that it binds to a different region of the substance being detected than does the first immunological binding partner.

In producing the region-specific polyclonal antibody, the process comprises:
(a) binding a substance to a carrier via one or more monoclonal antibodies specific for an epitope on said substance, said monoclonal antibody and said substance being firmly bound to said carrier;
(b) binding a polyclonal antibody specific for said carrier-bound substance;
(c) washing said bound polyclonal antibody;
(d) eluting bound polyclonal antibody from said substance under conditions such that said monoclonal antibody and said substance remain bound to said carrier; and
(e) recovering said region-specific polyclonal antibody.

The specific concentrations of monoclonal antibody, substance bound to the monoclonal antibody, and polyclonal antibody, as well as such parameters as incubation temperature and time for binding of polyclonal antibodies, and elution conditions, can be varied.

For example, the substance-specific polyclonal antibody can be absorbed to the substance bound to the carrier by incubating the polyclonal antibody and substance at 4°-37° C. for up to 72 hours. The absorbed polyclonal antibody can then be eluted from the carrier bound substance by such common techniques as use of an acidic solution, such as 0.1–1.0 M glycine-HCl buffer at pH 2.0–5.0, or a chaotropic agent, such as 1.0–5.0 M potassium thiocyanate at pH 4.0–7.5.

Several substances can be detected by the methods of the invention, among them exogenous, endogenous and other substances.

The term "exogenous substance" as used in the invention is meant to include any substance which is not normally present in the source as well as natural substances artificially introduced to the specimen. Examples of exogenous substances not normally present in the source from which the sample is taken are antigens derived from such pathogenic sources as viruses, bacteria, and parasites. An example of natural substances which are artificially introduced to the source of the specimen would be biological response modifiers such as the interferons or interleukins.

Substances which are "endogenous" are those which originate in the source from which, the sample is taken. Examples of such endogenous substances would be hormones, steroids, lipids, enzymes, and receptors, the levels of which could give an indication of the overall status of the source of the sample.

Haptens are small molecules that do not by themselves induce antibody production, but are capable of being bound by an antibody molecule. However, it is possible to produce antibody to a hapten if the hapten is first linked to a carrier before immunization.

For purposes of the invention, a drug could be any substance for which the term is commonly used, such as, for example, antibiotics, as well as such substances as biological response modifiers.

An antigen is a substance which is capable of inducing antibody production. Antigens are found throughout nature and may be derived from many different sources One source of antigens are those found associated with pathogens. A pathogen may be, for example, any virus, bacteria, or parasite, which is capable of causing disease.

Still other substances which can be detected using the invention are hormones, steroids, lipids, and enzymes.

Hormones are substances that act to inhibit or excite metabolic activities. Examples of hormones of considerable interest are those associated with reproduction, such as human choriogonadotropin, leutinizing hormone, prolactin, and follicle stimulating hormone, as well as hormones associated with growth, such as human growth hormone, somatomedin, and thyroid stimulating hormone and other hormones such as parathyroid hormone, adrenocorticotropic hormone, vitamin D and its metabolites, and calcitonin.

Steroids have a basic chemical structure of cyclopentenoperhydrophenanthrane. Certain steroids play a crucial role in overall biological activity. Among the most important steroids are cortisol, aldosterone, progesterone, estradiol, and testosterone.

Lipids are water-insoluble organic substances which are extractable by non-polar solvents such as chloroform, ether and benzene. Among the classes of lipids of biological significance are the neutral fats, phosphoglycerides, glycolipids, and cholesterol esters. Of particular importance are cholesterol, lecithin, carotene, sphingomyelin, cerebroside, and ganglioside.

Enzymes are protein molecules which catalyze biochemical reactions. Enzymes are so significant in maintaining a homeostatic environment that they effectively represent intermediate metabolism within the organism. Changes in the concentration of enzymes which are associated with certain biochemical pathways can be of valuable diagnostic significance in evaluating a disease state. Examples of enzymes of significance are urease, deoxyribunuclease, ribonuclease, creatinine phosphokinase, lactic dehydrogenase, glutamic oxaloacetic transaminase, alkaline phosphatase, 5'-nucleotidase, aspartate aminotransferase, alanine aminotransaminase, and gamma-glutamyl transpeptidase.

The levels of antibodies present in a specimen can sometimes give an indication of factors to which the host immune system has recently been exposed. In humans, antibodies are divided into five classes delineated IgG, IgM, IgA, IgD, and IgE. IgE is associated predominantly with the allergic response. An allergic response is mediated by IgE through its interaction with certain sensitizing substances which are known as allergens. When the allergen binds to IgE molecules localized on mast cells, a series of events occurs which manifests itself in the symptoms which are commonly associated with allergies. While it is possible to measure the total level of IgE in a specimen and from this information determine, in general, whether a patient is having an allergic response to some allergen, it is of much greater clinical value to be able to determine the exact allergen which is causing the allergic response. This can be done by determining whether or not a specimen contains IgE antibodies specific for, and capable of binding to, a given allergen.

The present invention thus also provides a method for the determination of allergen-specific IgE in a sample, which comprises:
(a) contacting a sample containing an allergen-specific IgE with:
  (i) a first immunological binding partner specifically reactive with said allergen-specific IgE, wherein the first immunological binding partner is bound to biotin or a biotin-binding protein, and
  (ii) a second immunological binding partner specifically reactive with said allergen-specific IgE, wherein said second immunological binding partner is detectably labeled;
(b) incubating the components of step (a) for a period of time and under conditions sufficient to form an immune complex consisting of said allergen-specific IgE, said first immunological binding partner, and said second immunological binding partner;
(c) contacting the sample containing said immune complex of step (b) with a biotin-binding protein or with biotin bound to a carrier for a period of time and under conditions sufficient for said complex to bind to said carrier;
(d) separating said carrier from the sample; and
(e) determining the detectably labeled second immunological binding partner in either said sample or said carrier;
wherein the reaction between said first immunological binding partner and said carrier occurs after, or substantially contemporaneously with, formation of an immune complex between said first immunological binding partner and said substance.

This technique can be used to detect allergen-specific IgE either directly in the sample or after the allergen-specific IgE has been substantially purified as, for example, by affinity chromatography.

The first binding partner in this instance is an allergen to which is bound either biotin or a biotin-binding protein such that the allergen remains capable of being bound by the allergen-specific IgE in the sample. The second binding partner is either one or more monoclonal antibodies or a polyclonal antibody specific for IgE. In addition, the second binding partner is detectably labeled. The carrier will have bound to it biotin if the first binding partner has a biotin-binding protein attached to it, or a biotin-binding protein if the first binding partner has biotin bound to it.

Biotin can be bound to allergen or allergen extracts using techniques common to those of ordinary skill in the art as, for example, by:
(a) mixing an antigen extract with N-hydroxysuccinimide biotin (NHS-biotin);
(b) incubating said mixture 4–24 hours, at 4°–37° C.;

(c) dialyzing said mixture to remove unreacted NHS-biotin.

The determination of allergen-specific IgE in a sample using the method according to the invention can be done in any of four modes previously described.

Examples of allergens or their extracts which can be detected in the immunoassay according to the invention are those derived from molds, fungi, parasites, pollens, animal dander, salivary proteins, drugs, toxins, and venoms.

The materials for use in the assay of the invention are ideally suited for the preparation of a kit. Such a kit may comprise a carrier means being compartmentalized to receive in close confinement one or more container means such as vials, tubes and the like, each of said container means comprising one of the separate elements to be used in the method.

For example, one of the said container means may comprise biotinylated monoclonal antibodies or biotinylated antigen. A second container may comprise soluble, detectably-labeled monoclonal antibody, region-specific polyclonal antibody, or polyclonal antibody in lyophilized form or in solution. The carrier means may also contain a third container means comprising a biotin-binding protein, such as avidin or streptavidin, bound to a carrier.

In addition, the carrier means may also contain a plurality of containers each of which comprises different, predetermined amounts of known antigen. These latter containers can then be used to prepare a standard curve into which can be interpolated the results obtained from the sample containing the unknown amount of antigen.

In using the kit all a user has to do is add, to a container, a premeasured amount of a sample containing the measurable, yet unknown amount of substance to be detected, the contents of the biotinylated first binding partner present in the first container, the contents of the labeled antibody present in the second container, and the contents of the third container which contains the carrier to which is bound a biotin-binding protein into the first container. Alternatively, the biotin-binding protein can be provided attached to the container to which the sample and the contents of the first and second containers are added. After an appropriate time for incubation, an immune complex is formed and is separated from the supernatant fluid, and the immune complex or the supernatant fluid are detected, as by radioactive counting or addition of an enzyme substrate, and color development.

As a general example, a sandwich immunoassay for human growth hormone (hGH) was carried out using a biotinylated monoclonal antibody to hGH as the first binding partner and an $^{125}I$ polyclonal antibody, reacting with regions of the hGH molecule different from that of the monoclonal antibody, as the second binding partner. The experiment was done in two formats, and the sensitivity of each in detecting hGH was compared.

In the first experimental format, the biotinylated monoclonal antibody was immobilized to an avidin coated plastic bead before being added (as in Katz, et al., U.S. Pat. No. 4,496,654), along with the $^{125}I$ polyclonal antibody, to the hGH containing sample. Under these conditions only the second binding partner is free in solution to react with hGH.

In the second protocol, the monoclonal antibody to hGH was not immobilized prior to addition to the hGH containing specimen, but instead was reacted free in solution along with the $^{125}I$ polyclonal antibody. These conditions allow both binding partners to freely react with any hGH present in the sample. The second protocol was the same as the first in all respects except that the biotinylated monoclonal antibody was not immobilized onto the avidin coated bead before addition to the sample containing hGH. The biotinylated monoclonal antibody, $^{125}I$ polyclonal antibody, and avidin coated bead were added simultaneously to the hGH containing specimen.

Quite surprisingly, the second protocol showed much greater sensitivity in detecting hGH present in the sample. This enhanced reactivity is probably due to the more optimal molecular kinetics of the system when all of the antibody molecules are free to react in solution, as opposed to the first protocol wherein some of the antibody molecules are restricted in their kinetics by being immobilized on the avidin coated solid phase bead.

Having now generally described this invention, the same will be better understood by reference to certain specific examples which are incorporated herein for purposes of illustration only and are not intended to be limiting of the invention unless specified.

EXAMPLE 1

Preparation of Region Specific Polyclonal Antibodies

One gram of CNBr-activated Sepharose-4B Pharmacia Fine Chemicals, Inc. was washed and swollen with a total of 200 mls of 1mM HCl in several aliquots for 15 minutes. This swollen gel was then washed with 20 mls of 0.1 M carbonate buffer, pH 8.3, which was immediately suctioned off. Next, the gel was transferred to a previously prepared protein solution containing 2 mg of affinity isolated rabbit anti-mouse IgG in 0.1 M carbonate buffer. This protein solution and gel mixture were allowed to mix end-over-end overnight at room temperature. The protein solution was then aspirated from the gel and the gel transferred to a blocking solution of 1.0 M ethanolamine, pH 8.0, and mixed end-over-end for three hours at room temperature. This solution was then aspirated from the gel and the gel was washed five times with alternating 20 ml aliquots of 0.1 M carbonate buffer and 0.2 M glycine-HCl, pH 2.3. The washed gel was then suspended in a solution of 1 mg of mouse monoclonal antibody to human growth hormone in 0.01 molar PBS/BSA buffer, pH 7.4 with end-over-end mixing overnight at room temperature. The solution was then aspirated from the gel and the gel washed with 50 mls of 0.01 M PBS/BSA buffer before being resuspended in a solution of 0.01 M PBS/BSA buffer containing 350 mcg of purified human growth hormone with end-over-end mixing overnight at room temperature. After this time, the solution was aspirated from the gel and the gel washed with 50 mls of 0.01 M $PO_4$, 0.15 M NaCl, 0.1% $NaN_3$, pH 7.4, and then 20 mls of 0.2 M triethanolamine, pH 8.3. The gel was then resuspended in 15 mls of 500 mg% dimethyl suberimidate dihydrochloride in 0.2 M triethanolamine, pH 8.3 with end-over-end mixing overnight at room temperature. The solution was aspirated from the gel and the gel washed ten times with alternating 20 ml aliquots of 0.01 M $PO_4$, pH 0.15 M NaCl, 0.1% $NaN_3$, pH 7.4 and 0.2 M glycine HCl, pH 2.3. The solution was aspirated from the gel and the gel washed with dilute HCl, pH 1.85, and then equilibrated with 0.01 M $PO_4$, 0.15 M NaCl, 0.1% $NaN_3$, pH 7.4. The affinity gel matrix can now be used for purification of region specific polyclonal antibodies to human growth hormone.

To purify region specific polyclonal antibodies using the affinity gel matrix, the gel is packed into a liquid chromatography column and equilibrated with 0.01 M PBS/BSA buffer, at pH 7.4. Antisera to human growth hormone is then passed over the column to allow binding to the human growth hormone to occur. The gel is then washed with 0.01 M PBS/BSA buffer and then distilled water until all unbound protein is removed. The antibody bound to the column is then eluted with 0.2 M glycine HCl, pH 2.3. This antibody solution is then immediately dialyzed against 0.01 M $PO_4$, 0.15 M NaCl, 0.1% $NaN_3$, pH 7.4, and concentrated to approximately 100 ug/ml. The antibodies which are affinity purified in this manner are region specific for those portions of the human growth hormone molecule which do not bind the mouse monoclonal antibody.

EXAMPLE 2

Determination of hGH in Samples Using the DESP of the Invention and Conventional Sandwich Immunoassays An experiment was done comparing the sensitivity of the DESP of the invention and conventional sandwich immunoassays in detecting the presence of hGH at various concentrations. Standard dilutions of hGH using a W.H.O. reference preparation were prepared in 0.01 M phosphate buffered saline (PBS) with 2.0% bovine serum albumin (BSA) at concentrations of 0, 0.5, 1.5, 5.0, 5.0, and 35.0 ng/ml.

In determining the sensitivity of the standard sandwich immunoassay in detecting the various levels of hGH in the samples, a commercially available monoclonal antibody which had been biotinylated was first immobilized to an avidin coated plastic bead before being added, along with the $^{125}I$ polyclonal antibody (prepared as described in Example 1), to the hGH containing samples in duplicate. The sample tubes were placed on a clinical rotator at 170 rpm for two hours at room temperature. At the end of this time, the beads were washed twice with a 0.1% Tween 80 in PBS solution.

In the case of the DESP assay, the avidin coated bead, biotinylated commercially available monoclonal antibody, and $^{125}I$ region specific polyclonal antibody were added simultaneously to the duplicate samples containing the various concentrations of hGH. Incubation and washings were carried out the same as for the standard sandwich immunoassay.

Figure 1:
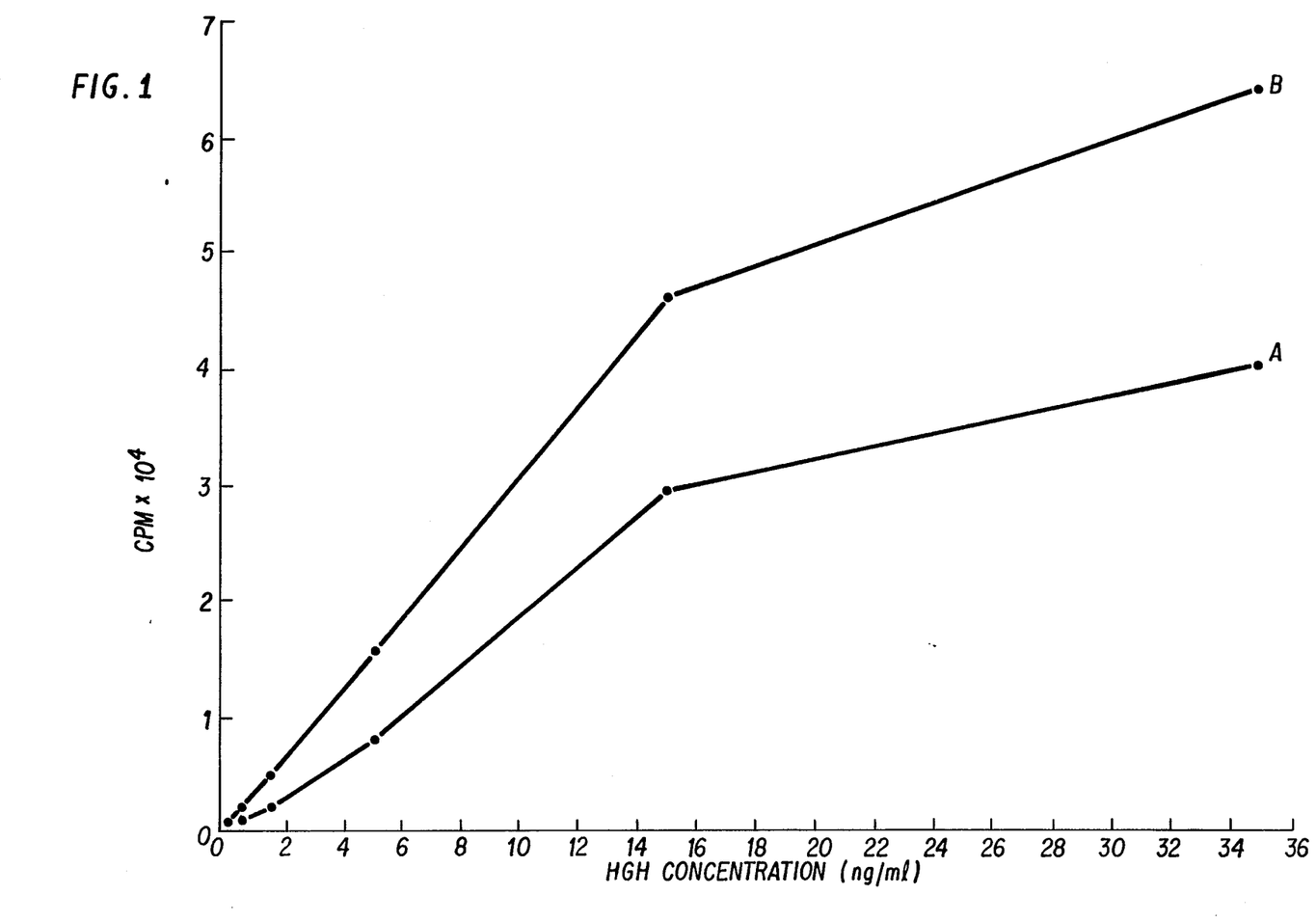
FIG. 1 shows the comparative response curves of a conventional sandwich immunoassay and a DESP immunoassay according to the invention for detecting hGH.

After washing, the duplicate beads from both of these assays were placed in a gamma scintillation counter to determine their relative radioactivity. The values obtained are presented in Table 1 and illustrated in FIG. 1.

TABLE 1

| [hGH[a]] | Conventional Sandwich Immunoassay[b] | Invention DESP Immunoassay[b] |
|---|---|---|
| 0.0 | 664 | 647 |
| 0.5 | 1167 | 1974 |
| 1.5 | 2275 | 4977 |
| 5.0 | 8153 | 15649 |
| 15.0 | 29553 | 46097 |
| 35.0 | 40615 | 64551 |

[a]concentration in ng/ml
[b]mean duplicate value in cpm

These results show that in this instance, the DESP immunoassay provides a greater overall sensitivity in detecting hGH than did the same reagents used in a conventional sandwich immunoassay.

EXAMPLE 3

Determination of hGH in Samples Using Three Different DESP Immunoassays

An experiment was done comparing the relative sensitivity of three different DESP immunoassays to detect hGH at various concentrations. The standard dilutions of hGH were prepared as described in Example 2.

In addition, the incubations, washings, and processing of the samples in these DESP immunoassays were done as described in Example 2. Table 2 shows the various immunological binding partners that were used in each of the three DESP immunoassays evaluated.

TABLE 2

| Assay | Biotinylated First Binding Partner | $^{125}I$-Labeled Second Immunological Binding Partner |
|---|---|---|
| A | Non-restricted polyclonal antibody | Non-restricted polyclonal antibody |
| B[a] | Monoclonal antibody-1 | Monoclonal antibody-2 |
| C | Monoclonal Antibody | Region-Specific Polyclonal Antibody[b] |

[a]Monoclonal antibody-1 and monoclonal antibody-2 react with different epitopes of hGH
[b]Prepared as in Example 1

Figure 2:
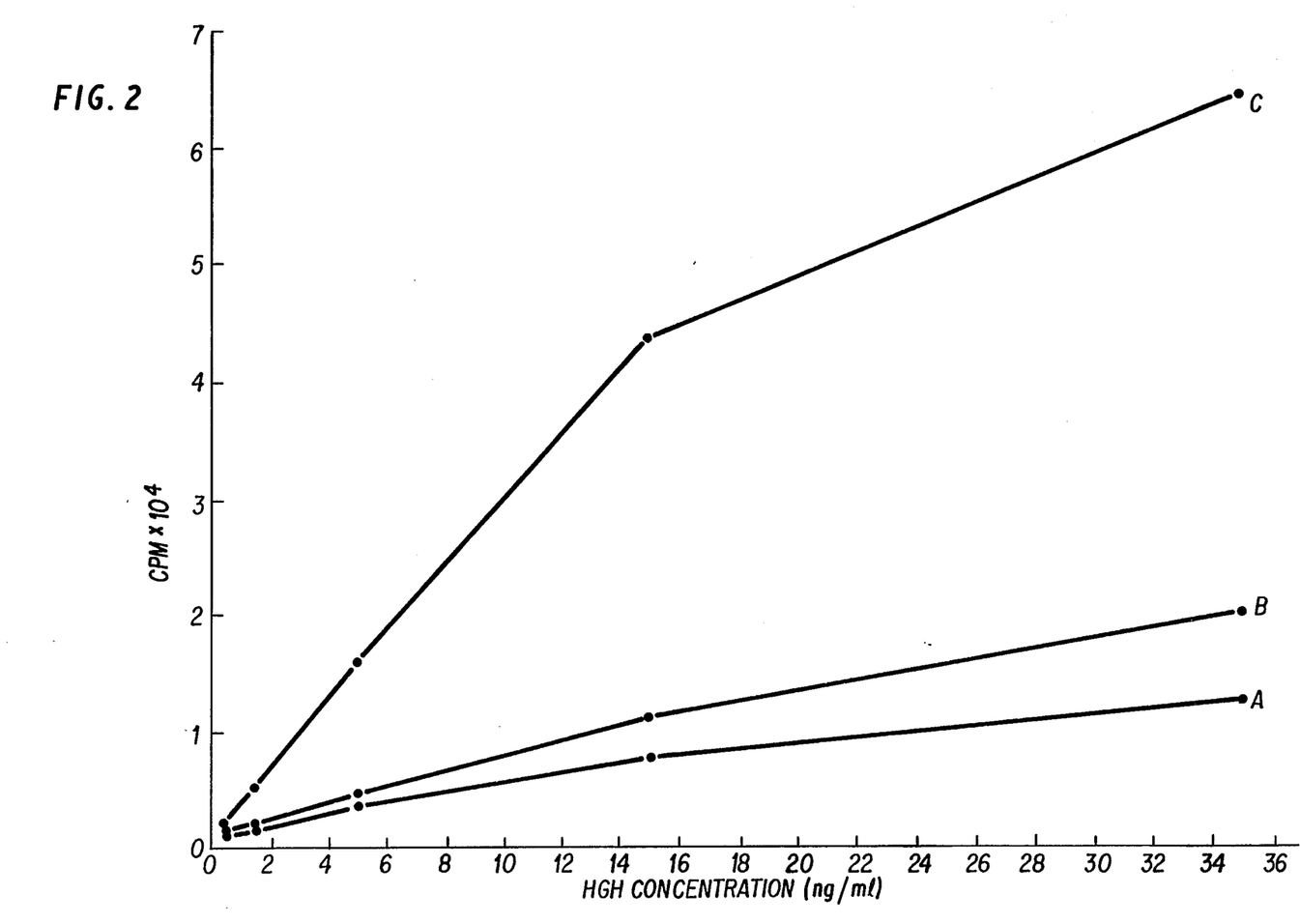
FIG. 2 shows the comparative response curves of three different DESP immunoassays in detecting hGH.

The data obtained using these three different DESP immunoassays are presented in Table 3 and graphically illustrated in FIG. 2.

TABLE 3

| [hGH[a]] | DESP Assay[b] | | |
|---|---|---|---|
|  | A | B | C |
| 0.0 | 594 | 613 | 647 |
| 0.5 | 851 | 1197 | 1974 |
| 1.5 | 1453 | 1880 | 4977 |
| 5.0 | 3522 | 4318 | 15649 |
| 15.0 | 7836 | 11018 | 46097 |
| 35.0 | 12644 | 20180 | 64551 |

[a]concentration in ng/ml
[b]mean duplicate value in cpm

The DESP assay utilizing biotinylated monoclonal antibody and radiolabeled region-specific polyclonal antibody (Assay C) was more sensitive in detecting hGH than either of the other two DESP assays tested. The bases for this difference in sensitivity can be hypothesized by considering the components of these other assays.

A major drawback to Assay A is that both the biotinylated and radiolabeled polyclonal antibody will compete for the same epitopic sites on the hGH molecule. Thus, while a greater number of labeled antibodies of different specificities are potentially available for binding, this will only occur if a given epitope is not first blocked by a biotinylated antibody specific for that same binding site.

On the other hand, the fact that the monoclonal antibodies used in Assay B are directed to different epitopic determinants on hGH means that in this assay there will be no competition between the biotinylated and radiolabeled antibody populations. However, because of the unlikely possibility that the epitope specific for the radiolabeled antibody will occur in great numbers on each hGH molecule, few radiolabeled monoclonal antibodies can bind to a given hGH molecule.

It is likely that assay C achieves the greatest sensitivity by combining signal intensification through the ability to bind many radiolabeled antibodies per hGH molecule, while avoiding epitopic competition between biotinylated and radiolabeled antibodies for the same binding sites on hGH by using region-specific radiolabeled antibodies non-competitive for the biotinylated monoclonal antibody binding site.

EXAMPLE 4

Determination of Allergen-Specific IgE in Samples Using Three Different Radioimmune Assays A study was done for purposes of comparing the sensitivity of three different radioimmune assays. These assays utilized avidin coated polystyrene beads, biotinylated allergen extract (Kentucky Blue Grass), and allergen-specific human IgE.

Biotinylation of the allergenic extract was done by taking one milliliter of Kentucky Blue Grass extract (1.0 mg/ml, Poa Pratensis, Hollister-Stier Lot No. K61798M) in 0.01 M $NaPO_4$, 0.15 M NaCl, 0.1% $NaN_3$, pH 7.4 to which was added 0.22 ml of a 6.4 mM solution of N-hydroxysuccinimidobiotin (Sigma MW 341) in N,N-dimethylformamide (Sigma MW 73.09). This mixture was incubated overnight (12-14 hours) at room temperature, then dialyzed against two 4 liter changes of 0.15 M NaCl at room temperature over an 8 hour period. This dialyzed biotinylated extract was stored at 4° C. until use.

Avidin coated polystyrene beads were prepared by first treating the beads (5/16 inch, Precision Plastic Ball, specular finish), with a 1% glutaraldehyde solution for at least 8 hours with gentle swirling on a rotator (70 rpm). After this time, the glutaraldehyde was removed and the beads washed 10 times with deionized water. The glutaraldehyde activated beads were then coated with a biotinylated bovine serum albumin solution (bovine serum albumin fraction V, Sigma) at a concentration of 10 ug biotinylated-BSA per bead in 0.01 M $NaPO_4$, 0.15 M NaCl, 0.1% $NaN_3$, pH 7.4 using 0.3 ml/bead for 8 hours with gentle swirling. At the end of this time, the beads were washed 10 times with deionized water. Next, the beads coated with biotinylated BSA were reacted with avidin (10 ug/0.03 ml/bead) in 0.01 M $NaPO_4$, 0.15 M NaCl, 0.1% $NaN_3$, pH 7.4 for 8 hours with swirling followed by washing 10 times with deionized water. The avidin coated beads were rinsed with 0.1% bovine serum albumin min in 0.01M $NaPO_4$, 0.15M NaCl, 0.1% $NaN_3$, pH 7.4 using 0.3 ml/bead for at least 2.5 hours with gentle swirling The beads were washed 10 times with deionized water followed by a final treatment with 2.5% sucrose in 0.15 M $NaPO_4$, 0.15 M NaCl, 0.1% $NaN_3$, pH 7.4, using 0.3 ml/bead for 30-60 minutes. The sucrose solution was drained and the beads allowed to dry at room temperature before storage at 4° C. until use.

Goat anti-human IgE (ATAB Atlantic Antibodies) was iodinated using the Chloramine-T method. The protocols followed for the three radioimmune assays were as follows: (1) Delayed Solid Phase (Forward Mode)

Biotinylated allergen extract (100 ul) at a concentration of 2.0 ug/ml in 0.1% BSA, 0.01 M $NaPO_4$, 0.15 M NaCl, 0.1% $NaN_3$ was combined with 100 ul of human serum containing elevated amounts of human allergen-specific IgE (D. Dunn, Inc.) at various RAST (radioallergosorbent test) units or 100 ul of horse serum (optically clear, Irvine Scientific). These solutions were mixed in 12×75 mm polystyrene plastic tubes for two hours at room temperature on a rotator (170 rpm). After this time, an avidin coated bead was added to each tube and the reaction continued for an additional 2 hours with rotation. At the end of this time, the tubes containing the avidin beads were washed three times with 2 ml of 0.01 M $NaPO_4$, 0.15 M NaCl, 0.1% Triton X-100, 0.1% $NaN_3$, pH 7.4. The presence of bound allergen-specific human IgE was detected by the addition of 200 ul of $^{125}$I goat anti-human IgE (1500 cpm/ul, 8.14 uCi/ug), followed by incubation for 2 hours at room temperature on a rotator (170 rpm). The duplicate tubes containing the beads were washed three times as above and counted for 1 minute in a gamma counter.

(2) Delayed Solid Phase (Simultaneous Mode)

This assay was run as described above for the forward mode except that the biotinylated allergen extract, the sample containing allergen-specific human IgE, and the avidin coated bead were combined simultaneously and incubated for 2 hours at room temperature with rotation (170 rpm). All other manipulations were carried out as described above for the forward assay.

(3) Immobilized Allergen

Each duplicate tube containing various concentrations of biotinylated allergen extract (100 ul at 2.0 ug/ml) was combined with 100 ul of horse serum and an avidin bead, and incubated for two hours at room temperature with rotation (170 rpm). After washing the tubes and beads as previously described, 100 ul of human serum containing allergen-specific IgE at various concentrations or 100 ul of horse serum, was added followed by the addition of 100 ul of 0.1% bovine serum albumin in 0.01 M $NaPO_4$, 0.15 M NaCl, 0.1% $NaN_3$, pH 7.4. The tubes were reincubated at room temperature for 2 hours with rotation (170 rpm) and washed as before. At the end of this time, 200 ul of $^{125}$I goat anti-human IgE was added to detect bound allergen-specific IgE and incubated with rotation (170 rpm) for 2 hours at room temperature.

Figure 3:
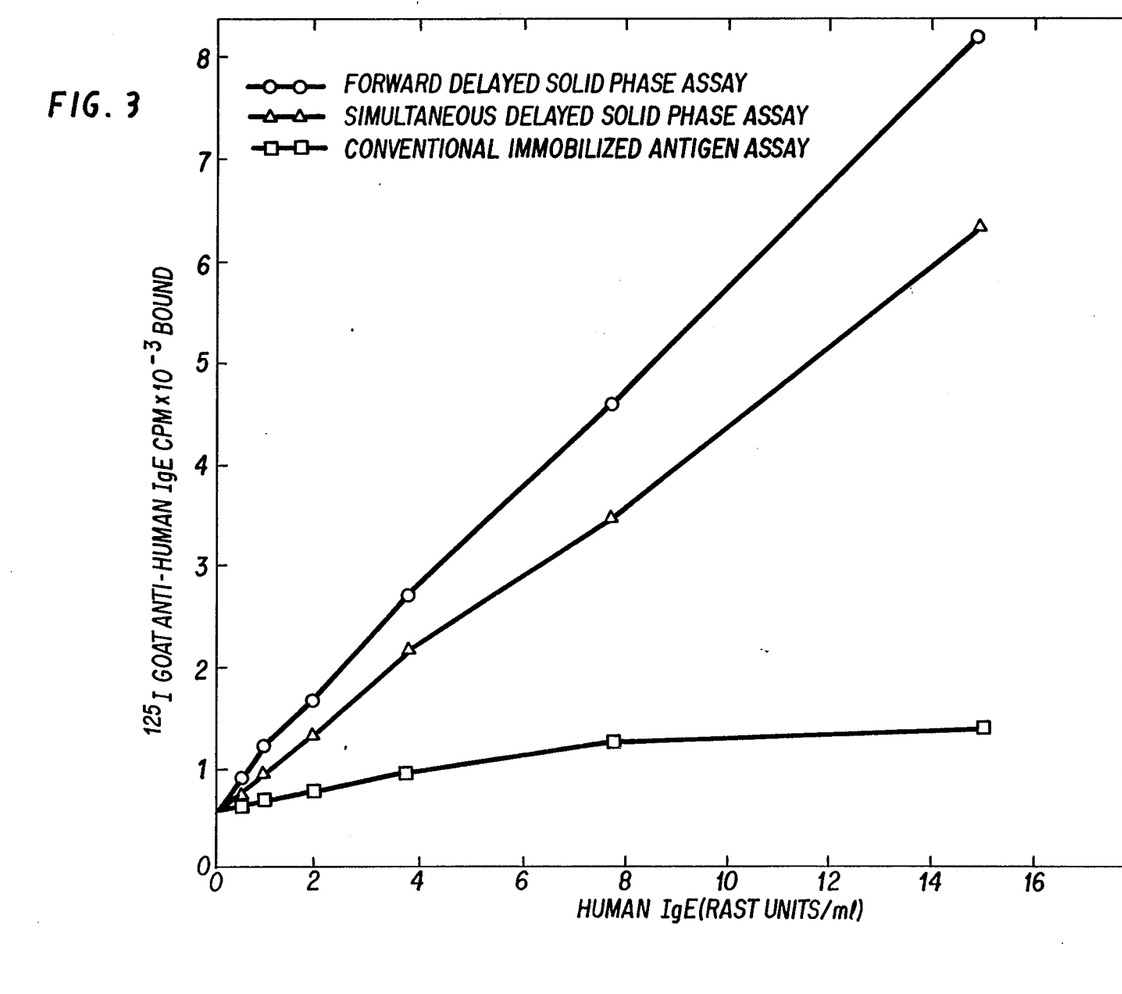
FIG. 3 shows the sensitivity of three different immunoassays detecting allergen-specific human IgE.

The results obtained using these three assays are presented in Table 4 and illustrated graphically in FIG. 3.

TABLE 4

| | Assay[b] | | |
|---|---|---|---|
| [human IgE][a] | Forward Delayed Solid Phase | Simultaneous Delayed Solid Phase | Conventional Immobilized Allergen |
| 15.0 | 8286 | 6388 | 1450 |
| 7.5 | 4600 | 3484 | 1280 |
| 3.75 | 2737 | 2181 | 955 |
| 1.88 | 1677 | 1322 | 744 |
| 0.94 | 1229 | 989 | 660 |
| 0.45 | 888 | 725 | 610 |
| 0.0[c] | 588 | 577 | 544 |

[a]concentration in RAST units/ml
[b]mean duplicate value in cpm
[c]horse serum control Both the forward and simultaneous delayed solid phase assays, in which the biotinylated allergen was free to react in solution with allergen-specific IgE prior to removal of this complex via the avidin coated bead, showed unexpectedly greater overall sensitivity than the conventional assay in which the allergen was first immobilized on the bead prior to exposure to the IgE containing sample. The increased sensitivity of the delayed solid phase assays can probably be attributed to a decrease in steric hindrance and an increase in molecular kinetics which cannot be achieved when the allergen is first restricted in these respects by binding to the solid phase as with the conventional immobilized allergen assay. The prior immobilization of the allergenic extract would require the migration of the allergen-specific IgE to the surface of the solid phase to which it is bound and may also preclude the availability of epitopic sites capable of being bound by the allergen-specific IgE molecule.

Having now fully described this invention, it will be readily apparent that the same can be performed within a wide and equivalent range of parameters, conditions, and the like, without affecting the spirit or scope of the invention or any embodiment thereof.

What is claimed as new and is desired to be covered by United States Letters Patent is:

1. A method of preparing a region specific polyclonal antibody to a substance capable of being bound by antibody and having at least two different epitopes, comprising the steps of:
   (a) binding said substance to a carrier via one or more monoclonal antibodies specific for an epitope on said substance, said monoclonal antibody and said substance being bound to said carrier under conditions which prevent their elution in step (d);
   (b) binding a polyclonal antibody specific for said substance to said carrier-bound substance;
   (c) washing said bound polyclonal antibody;
   (d) eluting said bound polyclonal antibody from said substance under conditions such that said monoclonal antibody and said substance remain bound to said carrier; and
   (e) recovering said region specific polyclonal antibody.

2. A method for the determination of a substance present in a sample, which comprises:
   (a) contacting said sample containing a substance having binding sites thereon capable of binding to at least two different immunological binding partners therefor with:
      (i) a first immunological binding partner to said substance, said partner being bound to biotin or a biotin binding protein;
      (ii) a detectably labeled, second immunological binding partner to said substance; and
      (iii) a carrier bound to a biotin binding protein or to biotin;
   wherein said first immunological binding partner is a monoclonal antibody and said immunological binding partner is a region specific polyclonal antibody prepared by the method of claim 1;
   (b) incubating the components of step (a) for a period of time and under conditions sufficient to form an immune complex between said substance, said first immunological binding partner, said second immunological binding partner, and said carrier;
   (c) separating the immune complex-carrier from the sample; and
   (d) determining the presence of such substance by determining the detectably labeled immunological binding partner in either the sample or the carrier.

3. A method for the determination of a substance present in a sample, which comprises:
   (a) contacting said sample containing a substance having binding sites thereon capable of binding to at least two different immunological binding partners therefor with a mixture of:
      (i) a first immunological binding partner to said substance, said first immunological binding partner being bound to biotin or a biotin binding protein; and
      (ii) a detectably labeled second immunological binding partner to said substance;
   wherein said first immunological binding partner is a monoclonal antibody and said second immunological binding partner is a region specific polyclonal antibody prepared by the method of claim 1;
   (b) incubating the components of step (a) under conditions sufficient to promote formation of an immune complex between said substance, said first immunological binding partner, and said second immunological binding partner;
   (c) contacting said complex of step (b) with;
      (iii) a carrier bound to a biotin binding protein or biotin under conditions sufficient to essentially irreversibly bind said immune complex to said carrier;
   (d) separating said carrier from the sample; and
   (e) determining the detectably labeled second immunological binding partner in either the sample or the carrier.

4. The method of claim 2 or 3, wherein said substance is exogenous to the source of said sample.

5. The method of claim 4, wherein said exogenous substance is a pathogen derived antigen.

6. The method of claim 5, wherein said pathogen derived antigen is of viral, bacterial, or parasitic origin.

7. The method of claim 2 or 3, wherein said substance is endogenous to the source of said sample.

8. The method of claim 7, wherein said endogenous substance is a hormone.

9. The method of claim 8, wherein said hormone is selected from the group consisting of human choriogonadotropin, luteinizing hormone, prolactin, follicle stimulating hormone, human growth hormone, somatomedin, thyroid stimulating hormone, parathyroid hormone, adrenocorticotropic hormone, vitamin D, and calcitonin.

10. The method of claim 7, wherein said endogenous substance is a lipid.

11. The method of claim 11, wherein said lipid is selected from the group consisting of cholesterol, lecithin, caroteine, sphingomyelin, cerebroside, and ganglioside.

12. The method of claim 7, wherein said endogenous substance is an enzyme.

13. The method of claim 12, wherein said enzyme is selected from the group consisting of urease, deoxyribonuclease, ribonuclease, creatinine phosphokinase, lactic dehydrogenase, glutamic oxaloacetic transaminase, alkaline phosphatase, 5'-nucleotidase, aspartate aminotransferase, alanine aminotransaminase, and gamma-glutamyl transpeptidase.

14. The method of claim 3, wherein said endogenous substance is an immunoglobulin.

15. The method of claim 2 or 3, wherein said detectable label is an enzyme.

16. The method of claim 15, wherein said enzyme is selected from the group consisting of maleate dehydrogenase, staphylococcal nuclease, delta-5-steroidisomerase, yeast alcohol dehydrogenase, alpha-glycerolphosphatedehydrogenase, triosephosphateisomerase, horseradish peroxidase, alkaline phosphatase, asparaginase, glucose-oxidase, beta-galactosidase, ribonuclease, urease, catalase, glucose-6-phosphate dehydrogenase, glucoamylase, and acetylcholinesterase.

17. The method of claim 2 or 3 wherein said detectable label is a radioactive isotope.

18. The method of claim 17, wherein said isotope is selected from the group consisting of $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$ and $^{75}Se$.

19. The method of claim 2 or 3, wherein said detectable label is a fluorescent compound.

20. The method of claim 19, wherein said fluorescent compound is selected from the group consisting of fluorescein isothiocyanate, rhodamine, phycoerythrine, phycocyanine, alophycocyanine, o-phthaldehyde, and fluorescamine.

21. The method of claim 2 or 3, wherein said detectable label is a chemiluminescent compound.

22. The method of claim 21, wherein said chemiluminescent compound is selected from the group consisting of luminol, isoluminol, aromatic acridinium ester, imidazole, acridinium salt, and oxalic ester.

23. The method of claim 2 or 3, wherein said detectable label is a bioluminescent compound.

24. The method of claim 2 or 3, wherein said bioluminescent compound is selected from the group consisting of luciferin and aequorin.

25. The method of claim 2 or 3, wherein said substance is prolactin or human growth hormone.

26. A kit useful for the detection of a substance in a sample comprising carrier means being compartmentalized to receive in close confinement therein one or more containers wherein:
    (a) a first container contains an immunological binding partner to said substance, said partner bound to biotin or a biotin-binding protein;
    (b) a second container contains an immunological binding partner to said substance, said partner bound to a detectable label;
    wherein said first immunological binding partner is a monoclonal antibody and said second immunological binding partner is a region specific polyclonal antibody prepared by the method of claim 11; and
    (c) a third container contains a solid phase to which a biotin-binding protein or biotin is bound.

27. The kit of claim 26, wherein said substance is an immunoglobulin.

28. The kit of claim 27, wherein said substance is IgE.

29. A kit useful for the detection of a substance in a sample comprising carrier means being compartmentalized to receive in close confinement therein one or more containers wherein:
    (a) a first container contains a water-soluble mixture of:
        (i) a first immunological binding partner to said substance, said partner bound to biotin or a biotin-binding protein; and
        (ii) a second, detectably labeled, immunological binding partner to said substance;
    wherein said first immunological binding partner is a monoclonal antibody and said second immunological binding partner is a region specific polyclonal antibody prepared by the method of claim 21, and
    (b) a second container contains a solid phase to which a biotin-binding protein or biotin is bound.

30. The kit of claim 29, wherein said first container (a) contains a mixture of biotin-bound monoclonal antibody to IgE, and region specific polyclonal antibody bound to an enzyme; and said second container (b) contains avidin-coated polystyrene beads.

31. An aqueous soluble composition comprising:
    a first immunological binding partner to a substance, said substance having binding sites thereon capable of binding to at least two different immunological binding partners, said first binding partner bound to biotin or a biotin-binding protein; and
    a second, detactably labeled, immunological binding partner to said substance;
    wherein said first immunological binding partner is a monoclonal antibody and said second immunological binding partner is a region specific polyclonal antibody prepared by the method of claim 1.

32. The composition of claim 3 which is in the form of a homogeneous aqueous solution.

33. A region specific polyclonal antibody to a substance prepared by the method of claim 1.

34. The region specific polyclonal antibody of claim 33 in detactably labeled form.

* * * * *

UNITED STATES PATENT AND TRADEMARK OFFICE
CERTIFICATE OF CORRECTION

PATENT NO. : 4,935,339

DATED : June 19, 1990

INVENTOR(S) : Richard Zahradnik

It is certified that error appears in the above-identified patent and that said Letters Patent is hereby corrected as shown below:

```
Claim 11, line 1, the claim dependency "11", should read --10--.
Claim 26, line 14, the claim dependency "11", should read --1--.
Claim 29, line 15, the claim dependency "21", should read --1--.
```

Signed and Sealed this

Twenty-seventh Day of August, 1991

Attest:

HARRY F. MANBECK, JR.

Attesting Officer

Commissioner of Patents and Trademarks